United States Patent

Kardos et al.

Patent Number: 5,885,789
Date of Patent: Mar. 23, 1999

[54] SOLUTION-BASED ASSAY FOR PEROXIDATIVELY-ACTIVE SUBSTANCES IN BODILY FLUIDS

[75] Inventors: Keith W. Kardos, Bethlehem; R. Sam Niedbala, Wescosville, both of Pa.

[73] Assignee: STC Technologies Incorporated, Bethlehem, Pa.

[21] Appl. No.: 825,670

[22] Filed: Mar. 20, 1997

Related U.S. Application Data

[60] Provisional application No. 60/013,966, Mar. 22, 1996.

[51] Int. Cl.⁶ ............................. C12Q 1/28; C12Q 1/00; G01N 33/53
[52] U.S. Cl. ........................ 435/28; 435/4; 435/975; 435/968; 436/63; 436/66; 436/74
[58] Field of Search ............... 435/28, 4, 975, 435/968; 436/63, 66, 74

[56] References Cited

U.S. PATENT DOCUMENTS

| | | | |
|---|---|---|---|
| 3,627,697 | 12/1971 | Rey et al. | 435/28 |
| 3,853,472 | 12/1974 | Rittersdorf et al. | 435/28 |
| 3,917,452 | 11/1975 | Rittersdorf et al. | 435/28 |
| 3,975,161 | 8/1976 | Svoboda et al. | 435/28 |
| 3,986,833 | 10/1976 | Mast et al. | 435/28 |
| 4,071,317 | 1/1978 | Lam | 435/28 |
| 4,071,318 | 1/1978 | Lam | 435/28 |
| 4,071,321 | 1/1978 | Lam | 435/28 |
| 4,148,611 | 4/1979 | Nand et al. | 435/28 |
| 4,220,713 | 9/1980 | Rittersdorf et al. | 435/28 |
| 4,310,626 | 1/1982 | Burkhardt et al. | 435/28 |
| 4,386,053 | 5/1983 | Motobayashi | 435/28 |
| 4,447,542 | 5/1984 | Gantzer | 435/28 |
| 4,556,640 | 12/1985 | Gantzer | 435/28 |
| 4,587,220 | 5/1986 | Mayambala-Mwanika et al. | 435/28 |
| 4,673,654 | 6/1987 | Talmage | 435/28 |
| 4,755,472 | 7/1988 | Ismail et al. | 435/28 |
| 5,081,040 | 1/1992 | Patel et al. | 435/28 |
| 5,182,213 | 1/1993 | Genshaw et al. | 435/28 |
| 5,318,894 | 6/1994 | Pugia | 435/28 |
| 5,362,633 | 11/1994 | Pugia | 435/28 |

FOREIGN PATENT DOCUMENTS

| | | |
|---|---|---|
| 0 043 469 | 1/1982 | European Pat. Off. . |
| 0 230 229 | 7/1987 | European Pat. Off. . |
| 0 253 548 | 1/1988 | European Pat. Off. . |
| 2 198 643 | 3/1974 | France . |

OTHER PUBLICATIONS

Jack R. Leonards, *J.A.M.A.*, vol. 179, No. 10, pp. 807–808 (1962).

V.R. Holland et al., *Tetrahedron*, vol. 30, pp. 3299–3302 (1974).

AMES ™ Reagent Strips Product Description.

*Primary Examiner*—Louise N. Leary
*Attorney, Agent, or Firm*—Morgan, Lewis & Bockius LLP

[57] ABSTRACT

A solution-based assay for determining the presence of peroxidatively-active substance in a bodily fluid is described. The solution-based assay contains a spectrophotometric substrate, a hydroperoxide, a pH 6.0–7.0 buffer, a surfactant, and a solvent such as DMSO, THF, DMF, or mixtures thereof, with the balance of the solution being water. The solution-based assay is particularly useful in qualitative and quantitative assays for urinary hemoglobin. Solution-based assay kits and assay methods are also described.

17 Claims, 1 Drawing Sheet

Hemoglobin

SOLUTION-BASED ASSAY FOR PEROXIDATIVELY-ACTIVE SUBSTANCES IN BODILY FLUIDS

This appln. claims the benefit of prov. appln. Ser. No. 60/013,966 filed Mar. 22, 1996.

FIELD OF THE INVENTION

The present invention relates to assays and methods to detect the presence of a peroxidatively-active substance in a bodily fluid. More particularly, the invention relates to a solution-based assay for detecting those substances, an assay kit, and a method of assaying bodily fluids for peroxidatively-active substances.

BACKGROUND OF THE INVENTION

Significant amounts of peroxidatively-active substances, such as blood or hemoglobin, are not normally present in bodily fluids. Such substances, particularly hemoglobin and its derivatives, often indicate abnormal bleeding which is symptomatic of various conditions, even cancer. To provide for early diagnosis, bodily fluids are often assayed to determine the presence, absence, or concentration of peroxidatively-active substances in bodily fluids.

In a diagnostic assay, a peroxidatively-active substance, like hemoglobin and its derivatives, causes a reaction between a hydroperoxide and an oxidizable spectrophotometric substrate or dye. The hydroperoxide releases oxygen which oxidizes the spectrophotometric substrate to yield a detectable change, e.g., a color change indicating the presence of the peroxidatively-active substance. In a quantitative assay, the intensity of that change may be used to determine the concentration of the peroxidatively-active substance in the bodily fluid test sample. Typical bodily fluids assayed include, for example, cerebral fluid, feces, gastrointestinal fluids, ocular fluid, saliva, serum, spinal fluid, vomit, or urine.

The presence of hemoglobin or blood in bodily fluids is generally termed "occult blood." When present, occult blood is not always apparent from visual examination. Occult blood may result from hemorrhages, tumors, ulcers, inflammations, disease or other injury of a particular organ or organs. Detecting occult blood permits diagnosis of a hemorrhage, other injury, or disease in, for example, the stomach, intestines, or urinary tract. The presence of blood in urine, for example, can indicate kidney or urinary tract damage. Normally, urine does not contain detectable amounts of blood.

Occult blood can appear in a bodily fluid as intact red blood cells or as free hemoglobin. In some situations, hemolysis of the red blood cells occurs after the cells have entered a bodily fluid, e.g., urine. Bodily fluid samples containing red blood cells also contain some hemolyzed occult blood.

Hemoglobinuria is the presence of free hemoglobin in the urine without red blood cells. In general, free hemoglobin from plasma is excreted by the kidney into the urine. Hematuria, in contrast to hemoglobinuria, is the presence of intact red blood cells in urine. Hematuria indicates a specific defect in the microscopic functional unit (the nephron) of the kidney. Hematuria may also indicate bleeding in the kidney, the ureter, the bladder or the urethra. Presently, differentiating between blood as cells versus free hemoglobin is generally considered to be of little diagnostic significance.

In urine, free hemoglobin may indicate that blood cells have ruptured due to traumatic passage through the kidney and urinary tract to the bladder. Urinary hemoglobin may also indicate that blood cells have been exposed to and hemolyzed by dilute urine in the bladder. Urinary hemoglobin, therefore, may indicate renal disorders, infectious diseases, neoplasms, or traumas to the urinary tract. More specifically, urinary hemoglobin can indicate a transfusion reaction, hemolytic anemia, or paroxysmal hemoglobinuria, or result from poisonings or severe burns. A positive urinary hemoglobin assay, without the presence of red cells, can indicate myoglobinuria as a result of traumatic muscle injury. Assays for urinary hemoglobin provide a vehicle for early diagnosis of such conditions.

Another peroxidatively-active substance, myoglobin, the red respiratory pigment of muscle tissue, is also not normally found in bodily fluids. Myoglobin is similar to hemoglobin in its composition and chemical reactions. Muscular injury can cause myoglobin to be discharged from muscle cells, to circulate in the plasma, and then be excreted in the urine. In addition, certain genetic muscle disorders can cause loss of myoglobin, which subsequently appears in the urine. Myoglobin may also be found in the urine after a cardiac infarct. The presence of myoglobin in urine is known as myoglobinuria. Assays capable of detecting myoglobin in bodily fluids, such as urine, can therefore provide significant diagnostic benefit.

As discussed, the presence of a peroxidatively-active substance in urine suggesting hematuria, hemoglobinuria, or myoglobinuria depends upon the nature and/or severity of the specific disorder, disease, or injury. Assays may also be used to test bodily fluids for other peroxidatively-active substances, such as leukocytes and bacteria. Overall, detecting a peroxidatively-active substance in a bodily fluid assists the early diagnosis of many disorders, diseases, injuries, and infections.

Traditionally, dry phase reagent strips, or dipsticks, have been used as assays for peroxidatively-active substances, as well as other analytes, in bodily fluids. A typical dry phase test strip is commercially available from Miles, Inc. under the trademark HEMASTIX®.

A reagent strip generally contains one or more test pads, having a porous carrier matrix, such as a paper matrix, impregnated with a buffered mixture of an organic hydroperoxide and an indicator dye, affixed to a plastic strip or handle. The reagent strip is dipped into a bodily fluid sample to test for the presence of analytes such as hemoglobin, or another peroxidatively-active substance. Exemplary dry phase reagent strips are described in U.S. Pat. Nos. 3,986,833; 3,917,452; 3,975,161; 4,587,220; 4,755,472; 5,318,894; and 5,362,633.

By changing color, a test pad indicates the presence of an analyte, such as hemoglobin or myoglobin, in the test sample. The color change intensity may be proportional to the concentration of the peroxidatively-active substance in the sample. Comparing the resulting test pad color to a standardized chart, an analyst can subjectively determine, the amount of an analyte, such as a peroxidatively-active substance, present in the sample.

Dry phase reagent strips, however, suffer from a number of disadvantages. Assays using reagent strips are quite labor intensive. As noted above, reagent strips require an analyst to conduct the test and match the color change with a chart and subjectively determine the quantity of an analyte in a test sample. Not only is this time consuming, but more importantly, it introduces the possibility of human error. In addition, a reagent strip often requires the results be read within a certain amount of time after testing. This creates an additional time pressure on an analyst and increases the possibility for human error and misdiagnosis. Finally, having multiple test pads on a single reagent strip exposes the possibility of cross-contamination of reagents during manufacture or testing. This possibility may compromise the reagent strip's diagnostic integrity.

A need exists, therefore, for an accurate assay of bodily fluids to test for peroxidatively-active substances. The assay should be capable of qualitative and/or quantitative analysis. The assay should be useable in clinical settings such as a clinical laboratory and in non-clinical settings such as a doctor's office or even at home. The assay should provide clear, reproducible detection and measurement of the peroxidatively-active substances in the bodily fluid permitting more accurate diagnosis and medical treatment. Use of the assay should be time efficient and have a low likelihood of error.

SUMMARY OF THE INVENTION

The present invention answers one or more of these needs by providing a solution-based assay for determining the presence of a peroxidatively-active substance in a bodily fluid, an assay kit, and an assay method.

In a first embodiment, the invention provides a solution-based assay for determining the presence of a peroxidatively-active substance in a bodily fluid. The solution-based assay comprises a spectrophotometric substrate, preferably present in an amount of 0.005–0.02 weight percent of the solution; a hydroperoxide, preferably present in an amount of 0.1–10 weight percent of the solution; a pH 6.0–7.0 buffer, preferably present in an amount of 0.1–20 weight percent of the solution; a surfactant, preferably present in an amount of 0.1–15 weight percent of the solution; a solvent selected from DMSO, THF, DMF, and mixtures thereof, preferably present in an amount of 0.1–10 weight percent of the solution; and water. This solution-based assay is particularly useful in automated assays for urinary hemoglobin.

A solution-based assay kit for determining the presence of a peroxidatively-active substance in a bodily fluid represents another embodiment of the invention. The kit may contain two or more, preferably three, separate stock reagents. The stock reagents may be mixed together to form a solution-based assay of the invention.

In a preferred embodiment, a first stock reagent comprises a spectrophotometric substrate, present in an amount of 5–20 weight percent of the solution, and a solvent selected from DMSO, THF, DMF, and mixtures thereof.

A preferred second stock reagent comprises a hydroperoxide, present in an amount of 0.1–10 weight percent of the solution; a surfactant, present in an amount of 0.1–15 weight percent of the solution; and a solvent selected from DMSO, THF, DMF, and mixtures thereof.

A third preferred stock reagent comprises a pH 6.0–7.0 buffer, present in an amount of 0.1–20 weight percent of the solution and water.

A further embodiment of the invention relates to an assay method for determining the presence of peroxidatively-active substances in a bodily fluid. The method provides a test sample of a bodily fluid, contacts the test sample with a solution-based assay composition of the invention, and detects a spectrophotometric change indicative of the presence, absence, or concentration of the peroxidatively-active substance in the test sample. This method, and the assays of the invention, may be automated and used for either qualitative or quantitative measurements.

DETAILED DESCRIPTION

Figure 1:
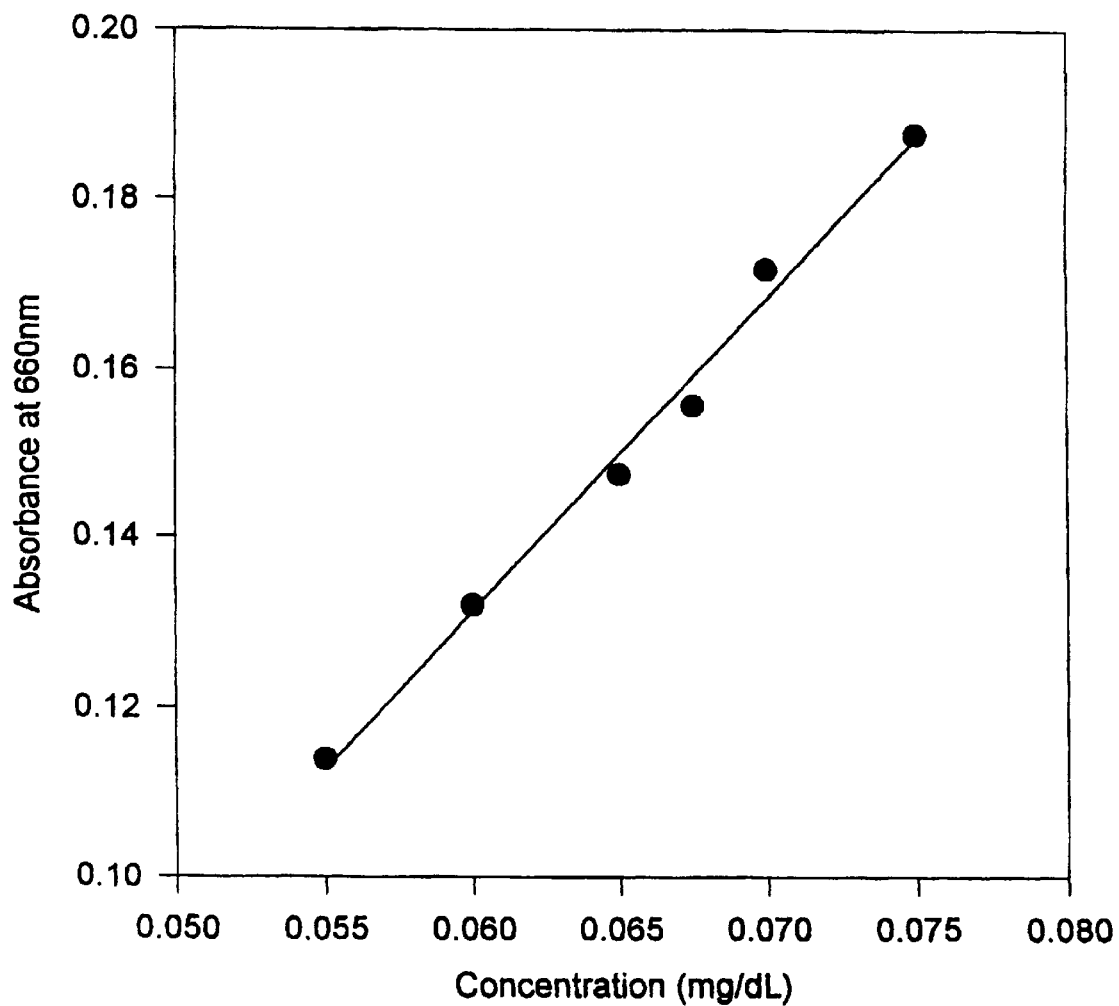
FIG. 1 is a calibration curve for a hemoglobin assay of the invention.

The assays and methods of the invention take advantage of the reactivity of a peroxidatively-active substance with a hydroperoxide to determine the presence or amount of peroxidatively-active substance in a bodily fluid. Unlike the dry phase reagent strips discussed above, the invention employs solution-based assays, avoiding the drawbacks associated with reagent strips. The assays and related methods may be used with any bodily fluid, such as cerebral fluid, feces, gastrointestinal fluids, ocular fluid, saliva, serum, spinal fluid, vomit, or urine.

To determine the presence or concentration of a peroxidatively-active substance in a bodily fluid, a test sample of the bodily fluid is contacted with a solution-based assay of the invention. If present, a peroxidatively-active substance, such as hemoglobin or occult blood, in the test sample reacts with a hydroperoxide from the assay to release oxygen. The oxygen then oxidizes a spectrophotometric substrate from the assay to give a detectable change, e.g. a color change, indicating the presence of the peroxidatively-active substance. Employing this chemistry, the solution-based assays and methods according to the invention may be used to qualitatively or quantitatively measure a peroxidatively-active substances in a bodily fluid. For quantitative measurements, the intensity of the detectable change is proportional to the concentration of the peroxidatively-active substance in the test sample, and accordingly, in the bodily fluid.

In one embodiment, the present invention provides a solution-based assay for determining the presence of peroxidatively-active substance in a bodily fluid. The assay comprises a spectrophotometric substrate, a hydroperoxide, a pH 6.0–7.0 buffering agent, a surfactant, a solvent selected from DMSO, THF, DMF, and mixtures thereof, and water.

Upon oxidation, the spectrophotometric substrate undergoes a detectable change, such as a color change, to indicate the presence of a peroxidatively-active substance in a bodily fluid test sample. The only limitation on the spectrophotometric substrate is its ability to exhibit a detectable change to indicate the presence of a peroxidatively-active substance. To be detectable, the change should at least be distinguishable spectrophotometrically, for example by absorbance spectroscopy. That is, the change should preferably be a change in the amount or type of light absorbed or emitted by an assayed test sample.

In a preferred embodiment, the detectable change is a color change which may be seen by the human eye. The spectrophotometric substrate may change from a colorless substrate to a colored product or vice versa, from colored to colorless. Assays yielding a deep colored response, a positive color change, are preferred.

For quantitative assays, the detectable change, preferably a color change, may be correlated with the peroxidatively-active substance concentration in the test sample and, thus, the bodily fluid. In a preferred embodiment, a color change proportional to the amount of peroxidatively-active substance present may be detected by absorbance spectroscopy.

Numerous spectrophotometric substrates may be used in an assay according to the invention. In general, the spectrophotometric substrate should be oxidized with relative ease to yield the detectable change indicating the presence of a peroxidatively-active substance. The spectrophotometric substance should also preferably be soluble in a solvent or preferably an aqueous media, such as the assay composition itself and particularly when combined with a bodily fluid.

Benzidine compounds, for example, represent preferred spectrophotometric substrates. When oxidized, benzidine compounds generally undergo a visible color change, for example, to a blue color. For quantitative assays, this color change can be detected using absorbance spectroscopy at about 600–670 nm range, with the peak absorbance at about 660 nm. As one of ordinary skill would appreciate, other color changes may be detected at appropriate wave lengths ranging from about 400–670 nm. Exemplary benzidine compounds include, but are not limited to, for example, benzidine; o-toluidine; 3,3',5,5'-tetra(lower alkyl)benzidine; odianisidine; 2,7-diaminofluorene; 3,3'-diaminobenzidine (DAB) and mixtures thereof and other suitable indicator dyes including, but not limited to, 2,2'-azino-bis(3-ethylbenz-thiazoline-6-sulfonic acid), o-phenylene-diamine; pyrogallol; and 4-amino-antipyrine. The term "lower alkyl" indicates a branched or unbranched $C_1$–$C_6$ alkyl group. These lower alkyl groups include, for example, methyl, ethyl, n-propyl, isopropyl as well as butyl, pentyl and hexyl groups and their isomers. The benzidine compound 3,3',5,5'-tetramethylbenzidine (TMB) is particularly preferred.

The amount of spectrophotometric substance present in the assay is, in general, limited only by the amount necessary for a detectable change. For a quantitative assay, the amount of spectrophotometric substrate should yield a measurable change in proportion to the amount of peroxidatively-active substance in the bodily fluid test sample. The spectrophotometric substrate may generally be present in the solution-based assay in an amount of 0.005–0.02 weight percent of the solution. More preferably, the spectrophotometric substrate is present in an amount of 0.007–0.012 weight percent of the solution and most preferably from about 0.009–0.010 weight percent. The spectrophotometric substrate may be present in amounts outside these general ranges depending on the intensity of its detectable change—particularly when that change is a color change.

A solution-based assay of the present invention also includes a hydroperoxide. As discussed above, in the presence of a peroxidatively-active substance, a hydroperoxide reacts to release oxygen. The oxygen, in turn, reacts with the spectrophotometric substrate causing a detectable change indicating the presence or concentration of a peroxidatively-active substance. Preferably, the hydroperoxide should be sufficiently reactive for the assay to detect one part of a peroxidatively-active substance in one trillion parts of bodily fluid test sample. The hydroperoxide should be sufficiently stable to avoid decomposition in the presence of the other assay components and during storage. Like the spectrophotometric substrate, the hydroperoxide should preferably be soluble in aqueous media, particularly when combined with a sample of a bodily fluid.

The hydroperoxide may be selected from many well known hydroperoxides. Suitable hydroperoxides include, but are not limited to, hydrogen peroxide, cumene hydroperoxide, t-butyl hydroperoxide, diisopropylbenzene hydroperoxide, 1-hydroxycyclohexane-1-hydroperoxide, paramenthane hydroperoxide, 2,5-dimethylhexane-2,5-dihydroperoxide, 1,4-diisopropylbenzene monohydroperoxide, p-t-butylisopropylbenzene hydroperoxide, 2-(alpha-hydroperoxyisopropyl)-6-isopropylnaphthalene, tetralin hydroperoxide, and combinations of these hydroperoxides. Hydrogen peroxide and cumene hydroperoxide are particularly preferred for use in a solution-based assay of the invention.

An assay of the invention should contain sufficient hydroperoxide to react with any peroxidatively-active substance present and cause a detectable change in the spectrophotometric substrate. The hydroperoxide is preferably present in the solution-based assay in an amount of about 0.01–10 weight percent of the solution. More preferably, the hydroperoxide is present from about 0.010–0.050 weight percent of the solution and most preferably from about 0.015–0.025 weight percent.

A solution-based assay according to the invention also contains a pH 6.0–7.0 buffer. Preferably, the assay has a buffered pH of about 6.5. Any buffer soluble in the assay composition may be used.

Preferably, the buffer is also soluble in the bodily fluid being assayed. Differences in pH may affect the assay conditions or reaction kinetics. For example, the spectrophotometric change, particularly color change, may be affected by pH changes. The absorbance maximum of a spectrophotometric substrate may vary with pH. This can readily be determined by running an absorption spectra and the assay performed using the new maximum. Alternatively, the detectable change may be slower to develop.

Exemplary buffers include, but are not limited to, acid buffers; citric acid buffers; tartaric acid buffers; salicylic acid buffers; sulfosalicylic acid buffers; citrate buffers; tartarate buffers; salicylate buffers; sulfosalicylate buffers; 2,2-bis(hydroxymethyl)-2,2',2"-nitrilotriethanol; and sulfonic acid buffers such as 1,4-piperazine bis(ethanesulfonic acid), and 3-[N-tris(hydroxymethyl)methylamino]-2-hydroxypropanesulfonic acid (TAPSO). Combinations of such buffers may also be used. A particularly preferred buffer is a sodium citrate/citric acid buffer.

The buffer is present in the solution-based assay in a sufficient amount to maintain the desired pH before and after combination with a bodily fluid test sample. The amount will depend on the particular buffer or combination of buffers used. In general, the buffer concentration ranges from about 0.1–20 weight percent of the solution, more preferably from about 2–15 weight percent, and most preferably, from about 9–11 weight percent.

To lyse cells present in a bodily fluid test sample, an assay of the invention also contains a surfactant or a mixture of surfactants. The surfactant may be a cationic, anionic, or nonionic surfactant as long as it is capable of lysing cells. The peroxidatively-active substances in a bodily fluid to be assayed are often contained within intact cells found in the test sample, e.g., hemoglobin in red blood cells. By lysing the cells, the surfactant liberates the peroxidatively-active substance permitting it to be assayed. The surfactant may also function to solubilize peroxidatively-active substances within a test sample. An assay of the invention should contain sufficient amounts of a surfactant to accomplish these functions.

The surfactant is preferably an anionic surfactant, such as a long carbon chain sulfate or sulfonate. Such preferred surfactants include, sodium lauryl sulfate, dioctyl sodium sulfosuccinate and sodium dodecylbenzene sulphonate, sodium octyl sulfate, t-octylphenoxypolyethoxy ethanol (e.g. TRITON® X-100, TRITON® X-405), polyoxyethylene (20) sorbitan monooleate, polyoxyethylene (20) sorbitan monolaurate, carbopol, with sodium lauryl sulfate being the preferred surfactant.

The surfactant is preferably present in the solution-based assay in an amount of about 0.01–15 weight percent of the solution. More preferably, the surfactant is preferably about 0.05–2 weight percent of the solution, and most preferably from about 0.07–0.15 weight percent.

An assay of the invention may also contain a solvent selected from DMSO, THF, DMF, and mixtures thereof. DMSO is the preferred solvent. The solvent functions to improve the solubility of other assay components. Water, preferably deionized water, generally constitutes the balance of a solution-based assay of the invention.

The assay preferably contains a sufficient amount of solvent to increase the solubility of other assay components, in the assay itself, and when combined with a bodily fluid. For health and cost reasons, excess solvent should preferably be avoided. Preferably, the bodily fluids being assayed should also be miscible in the solution-based assay composition. The solvent may also assist in this miscibility. This is particularly true for quantitative assays where the concentration of a peroxidatively-active substance is determined by solution spectroscopy.

Generally, an assay contains about 0.1–10 weight percent of a solvent based on the weight of solution. Preferably, the solvent is present in an amount of 2–7 weight percent, and more preferably, in about 5 weight percent.

A solution-based assay of the invention may also contain an electron transfer agent. The electron transfer agent may be included to assist in the redox reaction between the peroxidatively-active substance and the hydroperoxide and/or the redox reaction between the hydroperoxide and the spectrophotometric substrate. Exemplary electron transfer agents, (also known as accelerators or promoters), known in the art include the quinolines and isoquinolines, and their derivatives. U.S. Pat. No. 3,853,472 discloses quinolines and isoquinolines useful as electron transfer agents and is hereby incorporated by reference. Specific compounds include, but are not limited to, isoquinoline, 4-bromoisoquinoline, 4-methylquinoline, 6-methoxyquinoline, 3-aminoquinoline and 5,6-benzoquinoline. Preferably, 4-methylquinoline, available under the brand name LEPIDINE® from Aldrich Chemical Co., Milwaukee Wis., may be used as the electron transfer agent.

A preferred solution-based assay of the invention generally contains an electron transfer agent in an amount of 0.01–10 weight percent of the solution. More preferably, the electron transfer agent may be present in an amount of about 0.01–2 weight percent of the solution and most preferably, from about 0.015–0.025 weight percent.

A second embodiment of the invention relates to a solution-based assay kit for determining the presence of a peroxidatively-active substance in a bodily fluid. Advantageously, the kit provides exceptional shelf life for an assay of the invention. The kit achieves this shelf life by separating the assay components discussed above into two or more stock reagents, preferably three stock reagents. The stock reagents may themselves be solutions of the assay components. The preferred embodiments for the specific assay components in the kit are the same as those discussed above. In general, the stock reagents may be stored cold for at least 12 months, preferably at temperatures of about 2°–8° C. Aqueous stock reagents may be stored at higher temperatures or even room temperature.

The stock reagents making up the kit may be mixed together prior to use as a solution-based assay of the invention. The resulting assay or "working reagent", a solution-based assay of the invention, also possesses an exceptional shelf life of approximately 10 days even when stored at room temperature, e.g., 20°–27° C.

In a preferred solution-based assay kit, a first stock reagent A comprises a solution of a spectrophotometric substrate. The stock reagent A generally contains the spectrophotometric substrate in an amount of 5–20 weight percent of the solution. A solvent selected from DMSO, THF, DMF, and mixtures thereof, constitutes the balance of the first stock reagent. Preferably, the spectrophotometric substrate may be present in concentrations ranging from about 7–13 weight percent of the solution, and more preferably, from about 9–10 weight percent. Preferably, the first stock reagent A has a volume of 1 ml. The first stock reagent A may be stored for extended periods of time in a refrigerator, preferably at temperatures of about 2°–8° C. The reagent may be a solid at these temperatures.

A second stock reagent B of the kit preferably contains other assay components. That is, the stock reagent B may contain a hydroperoxide, present in an amount of about 0.1–10 weight percent of the solution; a surfactant, in an amount of about 0.1–15 weight percent of the solution; and a solvent selected from DMSO, THF, DMF, and mixtures thereof, constituting the balance of the second stock reagent B. In a preferred embodiment, the stock reagent B contains the hydroperoxide in an amount of about 1–5 weight percent of the solution and the surfactant in an amount of 3–12 weight percent. More preferably, the stock reagent B contains the hydroperoxide in an amount of about 2–3 weight percent of the solution and the surfactant in an amount of 6–8 weight percent. The preferred volume of stock reagent B is 14 ml. Like the first stock reagent A, the second stock reagent B may also be stored cold for extended periods of time, preferably in a refrigerator, at temperatures of about 2°–8° C. At these temperatures, the reagent may be a solid.

A preferred third stock reagent C may be used as a diluent for the other two stock reagents. Preferably, this third stock reagent C is an aqueous solution of the assay's buffer. The buffer is generally present in the third stock reagent C in an amount of about 0.1–20 weight percent with the balance being water, preferably deionized water. The buffer is preferably present in an amount of about 5–15 weight percent and more preferably in about 9–11 weight percent. The stock reagent C is preferably made up in 1 L quantities.

Using a kit of the invention, the stock reagents may be mixed in any order to prepare a solution—based assay of the invention. A preferred method of preparing a solution-based assay, or a "working reagent" comprises the following steps:

1. Allow the reagents to come to room temperature (about 20°–27° C.). Stock Reagents A and B may be solids at storage temperatures of 2°–8° C., but generally become liquid at temperatures above 18° C.

2. Combine the preferred volumes of Stock Reagents A and B and mix gently for 1–2 minutes. Preferably, Stock Reagent B is poured into Stock Reagent A.

3. Combine the Stock Reagent A/B solution with the preferred volume of Stock Reagent C and mix gently for 30 minutes. This yields a Working Reagent according to the invention. Preferably, the Stock Reagent A/B is poured into Stock Reagent C.

4. Allow the Working Reagent to equilibrate sufficiently by incubating at room temperature (about 20°–27° C.) prior to use, preferably for about 8–24 hours.

As noted above, the preferred Stock Reagents A and B may contain dimethyl sulfoxide, DMSO. Therefore, caution should be exercised such as wearing gloves and avoiding skin contact, when handling these solutions.

In another embodiment, the present invention also relates to an assay method for determining the presence of peroxidatively-active substances in a bodily fluid. The assay method provides a test sample of a bodily fluid, and contacts the test sample with a solution-based assay composition of the invention. Detecting a spectrophotometric change in the combined assay/test sample indicates the presence of a peroxidatively-active substance in the bodily fluids. As discussed above, the lack of a detectable change indicates that the bodily fluid does not contain at least a certain threshold level of a peroxidatively-active substance. The threshold level may be set at different levels for different peroxidatively-active substances and bodily fluids. Generally, the threshold level should be low enough to detect abnormal levels of the peroxidatively-active substance in the bodily fluid, but high enough that "normal" amounts of such substances do not cause false positives. The amount of components in the assay, particularly the spectrophotometric substrate and hydroperoxide, may be adjusted to cause a detectable change only at or above the desired threshold. These amounts may be readily determined by calibrating the assay against standard solutions of a peroxidatively-active substance, as is known in the art. In a qualitative assay, only the amount of assay components to provide a detectable change may be needed. For quantitative measurements, the intensity of the spectrophotometric change is measured to determine the concentration of the peroxidatively-active substance in the bodily fluid. Thus, increased amounts of assay components may be necessary for a complete range of possible concentrations.

The samples of the bodily fluids may be obtained using known techniques. The samples may be assayed as fresh samples or after storage as long as sample integrity is maintained. The samples may also be filtered to remove large particulates that could interfere with the assay.

The solution-based assays and methods of the invention may be used for clinical or non-clinical testing of bodily fluids. Preferably, the assays may be used in a clinical laboratory with spectrophotometric instruments, particularly auto-analyzers. For both qualitative and quantitative assays, the assay may preferably be run on any spectrophotometric auto-analyzers, typically found in a clinical laboratory. A preferred auto-analyzer should have several basic features and permit automation of the assay method. The auto-analyzer should preferably be able to accurately pipette all reagents and test samples. It should also preferably measure and report all absorbances as they relate to the quantity of peroxidatively-active analyte in the sample. Suitable auto-analyzers include, but are not limited to, the Cobas-Bio auto-analyzer available from Roche Diagnostics and the Hitachi 747 auto-analyzer available from Boerhinger Mannheim, Atken, Germany. Calibrations may be done using standard solutions of a particular peroxidatively-active substance and a solution-based assay of the invention using standard procedures or as recommended by the auto-analyzer manufacturer.

The following discussion illustrates an assay method of the invention by describing a specific exemplary embodiment of the invention, an assay for urinary hemoglobin. For other bodily fluids, samples may be obtained using techniques commonly practiced in the art. Other peroxidatively-active substances may be assayed using similar solution-based assays and the general assay method.

Freshly voided urine specimens should be collected in clean, preferably and chemically inert sterile, plastic or glass sample containers. If not analyzed immediately, the specimens may be refrigerated (preferably at about 2°–8° C.) for up to about three days with as little dead-air space in the sample container as possible. To store specimens longer than three days, they should be kept frozen and then thawed before use. Test samples should be at room temperature (about 20°–27° C.) for testing. Test samples should also preferably have a pH of about 5–8. Fresh or properly stored urine specimens generally fall within this range. Preservatives are generally not required with urine specimens. Adulteration of urine specimens may cause erroneous results. If adulteration is suspected, another sample should be obtained.

A working reagent may be prepared using the general procedure described above, which is also illustrated in Example I below. For a urinary hemoglobin assays such as described below, 3,3',5,5'-tetramethylbenzidine (TMB), which gives a blue color change at about 660 nm, is the preferred spectrophotometric substrate.

A urine test sample, generally about 15 microliters, and an assay composition, about 250 microliters of a "working reagent" such as described in Example 1. The urine test sample and "working reagent" are allowed to fully react before detecting the spectrophotometric change indicating whether the urine specimen contains hemoglobin. Generally, the reaction is complete after about 2 minutes, but sufficient time should be allowed for complete reaction. Reaction times may vary with particular peroxidatively-active substance, bodily fluid, or assay composition. Where the spectrophotometric change is a color change, the reaction may be considered complete when the color becomes constant.

In a preferred assay, the urine test sample and working reagent may be transferred to a temperature-controlled sample wheel of a spectrophotometric auto-analyzer. The urine test sample and the working reagent are combined, allowed to mix, and react during rotation of the sample wheel, (prior to detection). Where the spectrophotometric substrate is TMB, the absorbance of the resulting solution may be measured at 660 nm to determine whether the urine sample contains any hemoglobin. In a quantitative assay, the absorbance value may be compared with calibrated data to determine the hemoglobin concentration.

Having described various embodiments of the invention, the following examples are provide to illustrate, not limit, the claimed invention.

EXAMPLE 1

An Assay and Assay Kit According to the Invention

The following stock reagents were prepared by mixing the various components at room temperature until dissolved.

| Stock reagent A: Component | Final Volume: 1 L Amount |
|---|---|
| 3,3',5,5'-tetramethylbenzidine (TMB) | 96 g |
| DMSO | 1 L |

3,3',5,5'-tetramethylbenzidine (TMB) was purchased from Boehringer Mannhiem, Atken, Germany.

| Stock reagent B: Component | Final Volume: 1 L Amount |
|---|---|
| Lauryl Sulfate | 71.43 g |
| LEPIDINE ® | 14.30 mL |
| Cumene hydroperoxide | 21.40 mL |
| DMSO | 1 L |

LEPIDINE® and cumene hydroperoxide, (80% pure), was purchased from Sigma Chemical Co., St. Louis, Mo.

| Stock reagent C:<br>Component | Final Volume: 1 L<br>Amount |
|---|---|
| 0.4 M Sodium Citrate<br>in deionized water | 980 mL |
| 0.4 M Citric Acid<br>in deionized Water | 20 mL |

To prepare the solution-based assay composition, 14 mL of stock reagent B was poured into 1 mL of stock reagent A and mixed gently for 1–2 minutes by stirring. The combined A/B reagent was poured into 1 L of stock reagent C and mixed gently by stirring for approximately 30 minutes and allowed to stand at room temperature overnight prior to use. This prepared a working solution-based assay composition to be used as a working reagent.

EXAMPLE 2

Calibration of the Working Reagent at 660 nm

A solution-based assay composition prepared according to Example 1 was used to calibrate its detectable color change having an absorbance at about 660 nm. Aqueous solutions of hemoglobin were prepared in the concentrations of 0.055, 0.060, 0.065, 0.068, 0.070, and 0.075 mg/dL. Twenty-one replicates of each hemoglobin solution were run using the following procedure.

The solution-based assay composition (or working reagent) and the hemoglobin solutions were equilibrated at room temperature before use. A 15 microliter sample of a hemoglobin solution and 250 microliters of the working reagent were transferred to the sample wheel of a Cobas-Bio autoanalyzer which was equilibrated at 37° C. The sample and the working reagent were mixed by rotation of the sample wheel. After the sample and working reagent were allowed to react for 2 minutes, the absorbance of the resulting solution was measured at 660 nm. The calibration curve shown in FIG. 1 was generated by plotting absorbance versus concentration data shown in Table 1 below and using standard regression analysis. This calibration curve can then be used to quantitatively assay the amount of hemoglobin in a bodily fluid.

TABLE 1

| HEMOGLOBIN CONC.<br>(mg/dL) | ABSORBANCE, 660 nm | REGRESSION<br>Conc. Absorb.<br>Coefficients: |
|---|---|---|
| 0.055 | 0.1139 | b(0): −0.09176 |
| 0.06 | 0.1319 | b(1): 3.717388 |
| 0.065 | 0.1474 | $r^2$: 0.990949 |
| 0.0675 | 0.1557 | |
| 0.070 | 0.1719 | |
| 0.075 | 0.1877 | |

The assay may also be run to qualitatively determine the presence of hemoglobin in a sample by using a specified cutoff concentration to distinguish positive (hemoglobin-containing) samples from negative samples. Suitable cutoff concentrations are in the range of 0.06–0.07 mg/dl. This allows the assay to be used for screening a large number of samples. Clinically positive samples may be submitted for cell count using known procedures to evaluate the number of red blood cells in the sample.

EXAMPLE 3

Urinary Hemoglobin Assay

A total of 564 human urine specimens were tested for urinary hemoglobin using a working reagent prepared as described in Example 1 in a solution-based urinary hemoglobin assay. The solution-based assay according to the invention was compared with a reagent strip assay using Ames™ Reagent Strips (Multistix®). The reagent strip assay is based on the peroxidase-like activity of hemoglobin to catalyze the reaction of diisopropyl benzene dihydroperoxide and 3,3',5,5'-tetramethyl benzidine. The resulting color change of the test strip ranges from orange through green, with high levels of blood (or hemoglobin) giving a blue color.

For the solution-based assay, a 15 microliter urine sample and 250 microliters of the working reagent were transferred to the sample wheel of a Cobas-Bio autoanalyzer which was equilibrated at 37° C. The sample and the working reagent were mixed by rotation of the sample wheel. After the sample and working reagent were allowed to react for 2 minutes, the absorbance of the resulting solution was measured at 660 nm with a cutoff value of 0.065 mg/dL. The reagent strips were dipped into the urine sample and read after about 60 seconds, according to the manufacturer's instructions. Positive results obtained by reagent strip were confirmed using microscopic examination.

The results of the assays are shown in Table 2, below. Of all specimens tested, 544 were found to be negative by both the solution-based assay of the invention and the Ames™ Reagent Strips (Ames™); 5 were found to be positive by the solution-based assay but negative by Ames™; 1 was negative by the solution-based assay but positive by Ames™; and 14 were positive by both the solution-based assay and Ames™. The 6 specimens exhibiting discrepancies between the two assays were not available for microscopic examination.

TABLE 2

| | Ames ™ Reagent Strips | |
|---|---|---|
| Solution-based Assay | + | − |
| + | 14 | 5 |
| − | 1 | 544 |

The claimed invention is:

1. A solution-based assay for determining the presence of a peroxidatively-active substance in a bodily fluid comprising:

a spectrophotometric substrate, present in an amount of 0.005–0.02 weight percent of the solution;

a hydroperoxide, present in an amount of 0.1–10 weight percent of the solution;

a pH 6.0–7.0 buffer, present in an amount of 0.1–20 weight percent of the solution;

a surfactant, present in an amount of 0.1–15 weight percent of the solution;

an electron transfer agent, present in an amount of 0.1–10 weight percent of the solution;

a solvent selected from DMSO, THF, DMF, and mixtures thereof, present in an amount of 0.1–10 weight percent of the solution; and water.

2. A solution based assay of claim 1, wherein the spectrophotometric substrate is selected from 3,3',5, 5'-tetramethylbenzidine, benzidine, and o-phenylenediamine, the hydroperoxide is selected from hydrogen peroxide and cumene hydroperoxide, the buffer is a sodium citrate/citric acid buffer, the surfactant is sodium lauryl sulfate, the solvent is DMSO, and the electron transfer agent is a benzoquinone.

3. A solution based assay of claim 1, wherein the peroxidatively-active substance is hemoglobin, and the bodily fluid is cerebral fluid, feces, gastrointestinal fluids, ocular fluid, saliva, serum, spinal fluid, urine, or vomit.

4. A solution based assay of claim 1, wherein the spectrophotometric substrate is selected from 3,3',5,5'-tetramethylbenzidine, benzidine, and o-phenylenediamine, the hydroperoxide is selected from hydrogen peroxide and cumene hydroperoxide, the buffer is a sodium citrate/citric acid buffer, the surfactant is selected from sodium lauryl sulfate, and the solvent is DMSO.

5. A solution-based assay of claim 4, wherein the peroxidatively-active substance is hemoglobin, and the bodily fluid is cerebral fluid, feces, gastrointestinal fluids, ocular fluid, saliva, serum, spinal fluid, urine, or vomit.

6. A solution-based assay kit for determining the presence of a peroxidatively-active substance in a bodily fluid comprising:

a first stock reagent comprising: a spectrophotometric substrate, present in an amount of 0.005–0.02 weight percent of the solution and a solvent selected from DMSO, THF, DMF, and mixtures thereof;

a second stock reagent comprising: a hydroperoxide, present in an amount of 0.1–10 weight percent of the solution; a surfactant, present in an amount of 0.1–15 weight percent of the solution; and a solvent selected from DMSO, THF, DMF, and mixtures thereof, and a third stock reagent comprising: a pH 6.0–7.0 buffer, present in an amount of 0.1–20 weight percent of the solution and water.

7. A solution-based assay kit of claim 6, wherein the second stock reagent further comprises an electron transfer agent, present in an amount of 0.1–10 weight percent of the solution.

8. A solution-based assay kit of claim 7, wherein the peroxidatively-active substance is hemoglobin, and the bodily fluid is cerebral fluid, feces, gastrointestinal fluids, ocular fluid, saliva, serum, spinal fluid, urine, or vomit.

9. A solution-based assay kit of claim 6, wherein the spectrophotometric substrate is selected from 3,3',5,5'-tetramethylbenzidine, benzidine, and o-phenylenediamine, the hydroperoxide is selected from hydrogen peroxide and cumene hydroperoxide, the buffer is a sodium citrate/citric acid buffer, the surfactant is selected from sodium lauryl sulfate, and the solvent is DMSO.

10. A solution-based assay kit of claim 9, wherein the peroxidatively-active substance is hemoglobin, and the bodily fluid is cerebral fluid, feces, gastrointestinal fluids, ocular fluid, saliva, serum, spinal fluid, urine, or vomit.

11. An assay method for determining the presence of peroxidatively-active substance in a bodily fluid comprising the steps of:

providing a test sample of a bodily fluid;

contacting the test sample with a solution-based assay for determining the presence of a peroxidatively-active substance in a bodily fluid comprising;

a spectrophotometric substrate, present in an amount of 0.005–0.02 weight percent of the solution;

a hydroperoxide, present in an amount of 0.1–10 weight percent of the solution;

a pH 6.0–7.0 buffer, present in an amount of 0.1–20 weight percent of the solution;

a surfactant, present in an amount of 0.1–15 weight percent of the solution;

a solvent selected from DMSO, THF, DMF, and mixtures thereof, present in an amount of 0.1–10 weight percent of the solution; and water; and detecting a spectrophotometric change indicative of the presence, absence, or concentration of the peroxidatively-active substance in the test sample.

12. An assay method of claim 11, wherein the peroxidatively-active substance is hemoglobin, the bodily fluid is cerebral fluid, feces, gastrointestinal fluids, ocular fluid, saliva, serum, spinal fluid, urine, or vomit, and in the solution-based assay:

the spectrophotometric substrate is selected from 3,3',5,5'-tetramethylbenzidine, benzidine, and o-phenylenediamine, the hydroperoxide is selected from hydrogen peroxide and cumene hydroperoxide, the buffer is a sodium citrate/citric acid buffer, the surfactant is selected from sodium lauryl sulfate, and the solvent is DMSO.

13. An assay method of claim 12, wherein the spectrophotometric change is a color change detected by absorbance spectroscopy at a wavelength ranging from 600 to 670 nm.

14. An assay method of claim 12, wherein the spectrophotometric change is a color change.

15. An assay method of claim 11, wherein the spectrophotometric change is a color change.

16. An assay method of claim 12, wherein the method is a quantitative method and the degree of spectrophotometric change is proportional to the amount of peroxidatively-active substance in the bodily fluid.

17. An assay method of claim 11, wherein the method is a quantitative method and the degree of spectrophotometric change is proportional to the amount of peroxidatively-active substance in the bodily fluid.

* * * * *